United States Patent [19]

Takematsu et al.

[11] 4,059,431
[45] Nov. 22, 1977

[54] PLANT GROWTH REGULATOR

[75] Inventors: Tetsuo Takematsu; Makoto Konnai, both of Utsunomiya; Makoto Takeda; Nobuhiko Fuga, both of Ami; Kaoru Ikeda, Utsunomiya; Kiyoshi Shugaya, Ami, all of Japan

[73] Assignee: Mitsubishi Petrochemical Co., Ltd., Tokyo, Japan

[21] Appl. No.: 690,779

[22] Filed: May 27, 1976

Related U.S. Application Data

[62] Division of Ser. No. 580,344, May 23, 1975.

[30] Foreign Application Priority Data

May 27, 1974 Japan .................................. 49-59491
Dec. 30, 1974 Japan .................................. 50-847
Apr. 28, 1975 Japan .................................. 50-50649

[51] Int. Cl.$^2$ ...................... A01N 9/36; C07C 143/68
[52] U.S. Cl. ...................... 71/87; 260/326 E; 260/448.2 B; 260/454; 260/456 R; 260/456 A; 260/456 P; C07D/295/16
[58] Field of Search ............... 260/454, 456 A, 456 P, 260/456 R; 71/87

[56] References Cited

U.S. PATENT DOCUMENTS 3,819,676  6/1974  Christensen et al. ............ 260/456 R

FOREIGN PATENT DOCUMENTS 756,099   8/1956   United Kingdom ............ 260/456 R
284,986   5/1971   U.S.S.R. ......................... 260/456 R
243,616   11/1969  U.S.S.R. ......................... 260/456 R Primary Examiner—Joseph Paul Brust
Attorney, Agent, or Firm—Wenderoth, Lind & Ponack

[57] ABSTRACT

A plant growth regulator comprising as an active ingredient a compound having a novel 2-sulfonyloxyethyl-phosphonic or -thionophosphonic acid skeleton of the formula

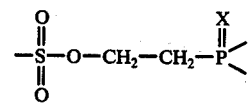

and a process for the production of the above compound.

A method for regulating the growth of plants which comprises applying the above regulator to plants or to the locus in which the plants are growing or will be grown.

7 Claims, No Drawings

PLANT GROWTH REGULATOR

This is a division of application Ser. No. 580,344 filed May 23, 1975.

This invention relates to a plant growth regulator comprising as an active ingredient a compound having a 2-sulfonyloxyethyl-phosphonic acid or 2-sulfonyloxyethyl-thionophosphonic acid skeleton of the following formula $$-\overset{O}{\underset{\underset{O}{\|}}{\overset{\|}{S}}}-O-CH_2-CH_2-\overset{X}{\overset{\|}{P}}\!\!<$$

wheren X is O or S.

Many phenomena in plants induced by ethylene, a simple hydrocarbon, have been discovered since a report was made at the end of the nineteenth century that putrefaction of apples during storage was caused by ethylene. About 40 years ago, it was found that ethylene is biosynthesized as a natural plant metabolite, and its importance has been recognized as a new physiologically active substance which dominates the physiological phenomenon of plants. This led to a rapid advance in the investigation of the physiological activities of ethylene in plants, and consequently, ethylene came into use for regulating the growth of plants. However, because ethylene is gaseous at room temperature, its acceptance in agriculture has been limited. In use, ethylene must be included in a closed receptacle or applied indoors, and cannot be directly applied to fields. Furthermore, it is not free from a danger of fire or explosion.

Later, ethylene-releasing substances which generate ethylene after application and thus can regulate the growth of plants were discovered, and it was reported that these substances exhibit various physiological activities on the growth of plants. These substances are called a plant growth regulator, and effectively used in the following applications.

1. Breaking of dormancy

The plant growth regulator breaks the dormancy of strawberries, grapes, and flowering plant bulbs to cause germination and flowering uniformly.

2. Increased yield in the sap

The ethylene-generating substance is most widely used for increasing the amount of the latex of rubber trees, and can increase an effect of promoting sap formation to almost twice as much. Accordingly, by spraying the ethylene-generating substance to old rubber trees with reduced ability to secrete latex, their secreting power can be markedly increased.

3. Acceleration of flowering

By spraying the plant-growth regulator to bananas and pipeapple trees, they can be cultivated in successive years, and the promoting of flower-set and the increased yield of both plants are expected.

4. Sex reversal

Pistil adhesion of cucumber, pumpkin and watermelon can be increased by application of the plant growth regulator, and an increase in their yield can be expected. In particular, the adhesion of pistil is poor in greenhouse cultivation of cucumber because of temperature trouble, but this drawback can be avoided by the application of the plant growth regulator.

5. Promotion of the ripening period

The plant growth regulator promotes the ripening period of many fruit trees such as pears, persimmon, apple, orange, peach or fig. As compared with the case of not treating the trees with the plant growth regulator, the ripening fruits can be shipped 5 to 20 days earlier. Accordingly, this greatly affects the distribution of the labor on harvesting and the cost of the fruits on shipment, thus leading to an increased profit.

6. Promotion of coloration

The plant growth regulator promotes the yellowing of tobacco leaves, and the coloration of oranges, apples and peppers, and products of uniform color can be harvested.

7. Promotion of the falling of leaves and fruits

The harvesting labor for picking leaves or fruits can be reduced by the application of the plant growth regulator. In particular, when it is applied to woods and bushes, it promote the falling of the leaves of shrubs of broad-leaved vines, and this can replace the cutting of these leaves.

It has previously been known that $\beta$-hydroxyethyl hydrazine or its derivative can be utilized as a plant growth regulator, and has an effect of promoting the ripening of unripen fruits (Japanese Patent Publication No. 10748/69). It has also been known that compounds having a 2-chloroethylphosphonic acid skeleton can be utilized as a plant growth regulator (British Patent Specification No. 1194433). On the other hand, U.S. Pat. No. 3,834,888 issued Sept. 10, 1974 discloses that compounds of the formula $$\overset{R^1}{\underset{R^2}{\diagdown}}\!\!\overset{\oplus}{S}-CH_2-CH_2-\overset{X}{\overset{\|}{P}}\!\!\overset{OH}{\underset{OH}{\diagup}}\quad A^{\ominus}$$

wherein $R^1$ and $R^2$ are a substituted or unsubstituted hydrocarbon group, X is S or O, and $A^-$ represents a non-phytotoxic anion, are useful as plant growth regulators.

We found that compounds having a skeletal structure of the formula $$-\overset{O}{\underset{\underset{O}{\|}}{\overset{\|}{S}}}-O-CH_2-CH_2-\overset{X}{\overset{\|}{P}}\!\!<$$

which are novel and not described in the prior literature exhibit superior plant growth regulating activities on a wide range of plants. For example, as will be shown hereinbelow by comparative examples, these compounds show superior results in plant growth regulating activity to 2-chloroethylphosphonic acid commercially available as a typical compound in the second prior art described above. Heretofore, the compounds having the above skeletal structure and their plant growth regulating activities have been completely unknown.

Accordingly, an object of this invention is to provide a superior plant growth regulator.

Another object of this invention is to provide a method for regulating the growth of plants using a compound having the above skeletal structure.

Still another object of this invention is to provide a process for preparing the above active compound. The above and other objects and advantages of this invention will become more apparent from the following description.

The active ingredient of the plant growth regulating composition of this invention is a 2-sulfonyloxy-ethylphosphonic acid- or 2-sulfonyloxyethyl-thionophosphonic acid derivative of the formula.

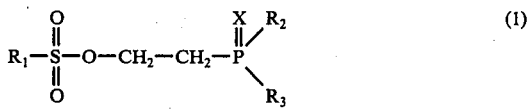

wherein $R_1$ is a group selected from the class consisting of substituted or unsubstituted alkyl groups, substituted or unsubstituted alkenyl groups and substituted or unsubstituted aryl groups; $R_2$ and $R_3$ are identical or different and represent a member selected from the class consisting of the group —OR' in which R' is a member selected from the class consisting of a hydrogen atom, substituted or unsubstituted alkyl groups, substituted or unsubstituted alkenyl groups and substituted or unsubstituted aryl groups, the group - SR' in which R' is the same as defined above, the group -N(R')$_2$ in which R' is the same as defined above or represents a morpholino group including N of the above group, the two R' groups being identical or different, and halogen atoms; and X is S or O, with the proviso that when X is O and both $R_2$ and $R_3$ are the group —OR', at least one of the groups —OR' is —OH, and when X is S, both $R_2$ and $R_3$ are not the groups —N(R')$_2$ at the same time.

In the above formula (1), $R_1$ is preferably selected from the class consisting of substituted or unsubstituted $C_1$ to $C_{12}$ linear-, branched- or cyclo-alkyl groups, substituted or unsubstituted $C_2$ to $C_{12}$ linear-, branched-, or cyclo-alkenyl groups and substituted or unsubstituted $C_6$ to $C_{14}$ aryl groups. Specific examples of the preferred $R_1$ are $C_1$ to $C_{12}$ linear or branched alkyl groups such as methyl, ethyl, n-propyl, iso-propyl, n-butyl, iso-butyl, sec-butyl, tert-butyl, pentyl, 2- methylpentyl, hexyl, heptyl, octyl, nonyl, decyl, undecyl, or dodecyl, and $C_5$ to $C_{12}$ cycloalkyl groups such as cyclopentyl, cyclohexyl, cyclooctyl or cyclodecyl.

When $R_1$ is a substituted alkyl group, the substituent is preferably selected from the class consisting of halogen atoms, a cyano group, a nitro group, alkoxy-carbonyl groups with the alkoxy moiety containing 1 to 12 carbon atoms, alkoxy groups containing 1 to 12 carbon atoms, a carboxyl group, acyl groups containing 1 to 12 carbon atoms, acyloxy groups containing 1 to 12 carbon atoms, a benzoyloxy group, a thiocyanate group, an isothiocyanate group, an acetamide group, a phthalimide group, an acetylthio group, a phosphono group, a sulfonyloxy group, a succinimide group, trialkylsilyl groups with the alkyl moiety containing 1 to 12 carbon atoms, aryl groups containing 6 to 14 carbon atoms, and alkylthio groups with the alkyl moety containing 1 to 12 carbon atoms. Specific examples of the preferred substituted alkyl groups include β-chloroethyl, γ-bromopropyl, γ-chloropropyl, γ,γ-dichloropropyl, chloromethyl, α-chlorocyclohexyl, β-cyanoethyl, β-methoxycarbonylethyl, β-ethoxycarbonylethyl, β-methoxycarbonylpropyl, γ-ethoxypropyl, γ-methoxypropyl, γ-phenoxypropyl, γ-ethoxyethyl, β-carboxyethyl β-carboxypropyl, β-acetylethyl, γ-acetoxypropyl, β-acetoxyethyl, γ-benzoylpropyl, β-benzoylethyl, γ-nitropropyl, β-nitroethyl, β-nitro-α-phenylethyl, γ-thiocyanatopropyl, β-thiocyanatoethyl, γ-isothiocyanatopropyl, β-isothiocyanatoethyl, β-phthalimidoethyl, β-succinimidoethyl, β-acetamidoethyl, β-acetylthioethyl, β-phosphonoethyl, 2-(β-phosphonoethyloxysulfonyl)ethyl, (β-phosphonoethyloxysulfonyl) methyl, γ-trimethylsilylpropyl, β-trimethylsilylethyl, benzyl, and βphenylethyl.

Specific examples of the preferred substituted branched alkyl group $R_1$ and 2-cyano-1-methylethyl, 2-chloro-1-methylethyl, 2-methoxyl, 1-dimethylethyl, 5-methyl-7-nitroheptyl, and 4-carboxy-3-methylbutyl.

Specific examples of the preferred substituted cycloalkyl groups are 4-chlorocyclohexyl, 4-cyanocyclohexyl, 4-methoxycyclohexyl, 4-ethoxycyclohexyl, 4-carboxycyclohexyl, 2-nitrocyclohexyl, and 4-chlorocyclooctyl.

In the formula (1), the alkenyl group represented by $R_1$ includes, for example, $C_2$ to $C_{12}$ linear or branched alkenyl groups such as vinyl, propenyl, allyl, isopropenyl, butenyl, butadienyl, pentenyl, hexenyl, octenyl, and dodecenyl, and $C_5$ to $C_{12}$ cycloalkenyl groups such as cyclopentenyl, cyclopentadienyl, cyclohexenyl, and cyclodecenyl. The alkenyl groups containing 5 to 12 carbon atoms are especially preferred.

The substituent for the alkenyl group $R_1$ is preferably the same as those described with respect to the substituted alkyl groups.

Examples of the preferred substituted alkenyl groups are β-chlorovinyl, γ-chloropropenyl, γ-cyanopropenyl, γ-nitropropenyl, chloroisopropenyl, γ-phenoxypropenyl, β-carboxyvinyl, β-methoxycarbonylvinyl, β-benzylvinyl, styryl, γ-succinimidopropenyl, γ-phthalimidopropenyl, γ-acetamidopropenyl, β-phosphonovinyl, and γ-trimethylsilylpropenyl.

The substituted cycloalkenyl group includes, for example, 4-chloro-2-cyclohexenyl or 4-carboxy-2-cyclohexenyl.

Examples of the aryl groups in formula (1) are phenyl, naphthyl, anthryl, phenanthryl, and biphenylyl. The substituent for the aryl groups includes, for example, an alkyl group containing 1 to 6 carbon atoms, a halogen atom, an acetyl group, an amido group, a nitro group, a cyano group, a carboxyl group, an alkoxy group containing 1 to 6 carbon atoms, a hydroxyl group, a sulfonyl group or a sulfo group. Specific examples of the substituted aryl groups in formula (1) are tolyl, xylyl, t-butylphenyl, cumenyl, chlorophenyl, bromophenyl iodophenyl, acetylphenyl, acetamidophenyl, nitrophenyl, cyanophenyl, carboxyphenyl, methoxyphenyl, ethoxyphenyl, chloronitrophenyl, bromonitrophenyl, chlorotoyl, nitrotolyl, carboxytolyl, chloromethoxyphenyl, cyanotolyl, hydroxyphenyl, nitronaphthyl, chloroanthryl, cyanophenanthryl, and methoxybiphenyl.

Preferably, $R_2$ and $R_3$ in formula (1) are selected from the class consisting of the groups —OR' in which R' is a member selected from the class consisting of a hydrogen atom, substituted or unsubstituted $C_1$ to $C_{12}$ linear-, branched- or cyclo-alkyl groups, substituted or unsubstituted $C_2$ to $C_{12}$ linear-, branched- or cycloalkenyl groups and substituted or unsubstituted $C_6$ to $C_{14}$ aryl groups, the groups -SR' in which R' is the same as defined above, the groups -N(R')$_2$ in which R' is the same as defined above or morpholino including N of the above group, and the two R' groups are identical or different, and halogen atoms, especially chlorine. Examples of R' in the groups -OR', -SR' and -N(R')$_2$ are the same as those mentioned with regard to group $R_1$.

Examples of the group -OR' are hydroxyl, methoxy, ethoxy, propoxy, isopropoxy, n-butoxy, tert-butoxy, dodecyloxy, cyclohexyloxy, benzyloxy, chloroethyloxy, phenoxy, chlorophenoxy, tolyloxy, allyloxy, and chloroallyloxy. Examples of the group -SR' are mercapto, methylthio, ethylthio, propylthio, isopropylthio, n-butylthio, tert-butylthio, dodecylthio, cyclohexylthio, benzylthio, chloroethylthio, phenylthio, chlorophenylthio, tolylthio, and allylthio.

Examples of the group -N(R')$_2$ are dimethylamino, isopropylamino, octylamino, dodecylamino, cyclopentylamino, cyclohexylamino, chloromethylamino, chloroethylamino, ethoxycarbonylmethylamino, cyanomethylamino, nitroethylamino, methoxymethylamino, chlorocyclohexylamino, phosphonomethylamino, phenylamino, tolylamino, cumenylamino, mesitylamino, xylylamino, chlorophenylamino, bromophenylamino, iodophenylamino, acetylphenylamino, acetamidephenylamino, aminophenylamino, naphtylamino, and morpholino groups.

Specific examples of the compounds of formula (1) are given below.

1. Compounds of formula (1-a)

$$R_1-\overset{O}{\underset{O}{\overset{\|}{\underset{\|}{S}}}}-O-CH_2-CH_2-\overset{O}{\overset{\|}{P}}\overset{OH}{\underset{OR'}{\diagdown}} \quad (1)\text{-a}$$

| Compounds No | R$_1$ | R' |
|---|---|---|
| 1 | 3-bromopropyl | methyl |
| 2 | chloromethyl | methyl |
| 3 | 2-cyanoethyl | methyl |
| 4 | 2-methoxycarbonylethyl | methyl |
| 5 | 2-methoxycarbonylethyl | isopropyl |
| 6 | 3-ethoxypropyl | methyl |
| 7 | 3-ethoxypropyl | hydrogen |
| 8 | 2-carboxyethyl | hydrogen |
| 9 | 2-acetylethyl | hydrogen |
| 10 | 3-acetoxypropyl | methyl |
| 11 | 3-benzoyloxypropyl | methyl |
| 12 | 2-nitroethyl | methyl |
| 13 | 2-nitro-1-phenylethyl | methyl |
| 14 | 3-thiocyanatopropyl | methyl |
| 15 | 2-isothiocyanatoethyl | methyl |
| 16 | 2-phthalimidoethyl | methyl |
| 17 | 2-phthalimidoethyl | hydrogen |

-continued

1. Compounds of formula (1-a)

$$R_1-\overset{O}{\underset{O}{\overset{\|}{\underset{\|}{S}}}}-O-CH_2-CH_2-\overset{O}{\overset{\|}{P}}\overset{OH}{\underset{OR'}{\diagdown}} \quad (1)\text{-a}$$

| Compounds No | R$_1$ | R' |
|---|---|---|
| 18 | 2-acetamidoethyl | methyl |
| 19 | 2-acetylthioethyl | methyl |
| 20 | 2-phosphonoethyl | hydrogen |
| 21 | $(HO)_2\overset{O}{\overset{\|}{P}}-CH_2CH_2-O-\overset{O}{\underset{O}{\overset{\|}{\underset{\|}{S}}}}-CH_2CH_2-$ | hydrogen |
| 22 | $(HO)_2\overset{O}{\overset{\|}{P}}-CH_2-CH_2-O-\overset{O}{\underset{O}{\overset{\|}{\underset{\|}{S}}}}-CH_2-$ | hydrogen |
| 23 | $(CH_3)_3Si-CH_2-CH_2-$ | hydrogen |
| 24 | benzyl | hydrogen |
| 25 | 2-carboxyethyl | butyl |
| 26 | 2-carboxyethyl | dodecyl |
| 27 | 2-carboxyethyl | 2-chloroethyl |
| 28 | 2-carboxyethyl | phenyl |
| 29 | 2-cyanoethyl | benzyl |
| 30 | 2-cyanoethyl | p-chlorophenyl |
| 31 | 2,3-dichloropropyl | methyl |
| 32 | 2,3-dibromopropyl | methyl |
| 33 | $(CH_3)_3\overset{\oplus}{N}\overset{Cl^\ominus}{\rule{1cm}{0.4pt}}CH_2-CH_2-$ | methyl |
| 34 | vinyl | methyl |
| 35 | allyl | methyl |
| 36 | cyclohexenyl | methyl |
| 37 | $H_2C=\underset{\underset{\text{\Large{C}}_6H_5}{\|}}{C}-CH_2-$ | methyl |
| 38 | methyl | hydrogen |
| 39 | methyl | ethyl |
| 40 | n-butyl | hydrogen |
| 41 | methyl | methyl |
| 42 | phenyl | hydrogen |
| 43 | p-tolyl | hydrogen |
| 44 | p-tolyl | ethyl |
| 45 | p-chlorophenyl | hydrogen |
| 46 | p-nitrophenyl | hydrogen |

(2) Compounds of formula (1-b)

$$R_1-\overset{O}{\underset{O}{\overset{\|}{\underset{\|}{S}}}}-O-CH_2-CH_2-\overset{S}{\overset{\|}{P}}\overset{R_2}{\underset{R_3}{\diagdown}} \quad (1\text{-b})$$

| Compounds Nos. | R$_1$ | R$_2$ | R$_3$ |
|---|---|---|---|
| 47 | methyl | —Cl | —Cl |
| 48 | p-tolyl | —Cl | —Cl |
| 49 | methyl | —OH | —OH |
| 50 | 2-carboxyethyl | —OH | —OH |
| 51 | methyl | —OCH$_2$—⌬ | —OCH$_2$—⌬ |
| 52 | p-tolyl | —OH | —OH |
| 53 | methyl | —SCH$_2$—⌬ | —SCH$_2$—⌬ |
| 54 | methyl | —OCH$_3$ | —S—C$_2$H$_5$ |
| 55 | methyl | —OCH$_2$—CH=CH$_2$ | —O—CH$_2$—CH=CH$_2$ |
| 56 | 2-carboxyethyl | —S—CH$_2$—CH$_2$—Cl | —S—CH$_2$—CH$_2$—Cl |

(3) Compounds of formula (1-c)

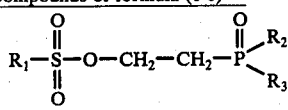

(excepting the case where $R_2$ is —OH, and $R_3$ is OR')

| Compounds Nos. | $R_1$ | $R_2$ | $R_3$ |
|---|---|---|---|
| 57 | methyl | —SCH$_2$—C$_6$H$_4$—Cl | —SCH$_2$—C$_6$H$_4$—Cl |
| 58 | methyl | —S—C$_6$H$_5$ | —S—C$_6$H$_5$ |
| 59 | methyl | —SCH$_3$ | —SCH$_3$ |
| 60 | p-tolyl | —S—C$_6$H$_5$ | —S—C$_6$H$_5$ |
| 61 | p-chlorophenyl | —S—C$_6$H$_4$—Cl | —S—C$_6$H$_4$—Cl |
| 62 | 3-chloropropyl | —SCH$_2$—C$_6$H$_5$ | —SCH$_2$—C$_6$H$_5$ |
| 63 | methyl | —SH | —SH |
| 64 | methyl | —OCH$_3$ | —SC$_2$H$_5$ |
| 65 | p-tolyl | —OCH$_3$ | —SCH$_2$—C$_6$H$_5$ |
| 66 | p-chlorophenyl | —OH | —SCH$_2$—C$_6$H$_5$ |
| 67 | 2-carboxyethyl | —OCH$_2$—CH=CH$_2$ | —S—CH$_3$ |
| 68 | methyl | —OCH$_3$ | —N(CH$_3$)$_2$ |
| 69 | 2-carboxyethyl | —OCH$_3$ | —N(C$_2$H$_5$)$_2$ |
| 70 | 2-methoxycarbonylethyl | —OH | —SCH$_3$ |
| 71 | 2-nitroethyl | —SCH$_3$ | —SCH$_3$ |
| 72 | vinyl | —OCH$_3$ | —SCH$_3$ |
| 73 | methyl | —N(CH$_3$)$_2$ | —N(CH$_3$)$_2$ |
| 74 | methyl | —NH—C$_6$H$_5$ | —NH—C$_6$H$_5$ |
| 75 | methyl | —NHCH(CH$_3$)$_2$ | —NHCH(CH$_3$)$_2$ |
| 76 | methyl | —NH—C$_6$H$_4$—Cl | —NH—C$_6$H$_4$—Cl |
| 77 | methyl | —N(CH$_3$)$_2$ | —NH—C$_6$H$_5$ |
| 78 | n-butyl | —NH—C$_6$H$_5$ | —NH—C$_6$H$_5$ |
| 79 | 2-chloroethyl | —NH—C$_6$H$_4$—Cl | —NH—C$_6$H$_4$—Cl |
| 80 | chloromethyl | —N(CH$_3$)$_2$ | —N(CH$_3$)$_2$ |
| 81 | p-tolyl | —NHCH(CH$_3$)$_2$ | —NHCH(CH$_3$)$_2$ |
| 82 | p-chlorophenyl | —NHCH(CH$_3$)$_2$ | —NHCH(CH$_3$)$_2$ |
| 83 | methyl | —N(morpholino) | —N(morpholino) |
| 84 | iso-propyl | —N(CH$_3$)$_2$ | —N(CH$_3$)$_2$ |
| 85 | 2-cyanoethyl | —NH$_2$ | —NH$_2$ |
| 86 | 2-methoxyethyl | —NHCH(CH$_3$)$_2$ | —NHCH(CH$_3$)$_2$ |
| 87 | methoxy | —NH$_2$ | —NH$_2$ |
| 88 | 2-phosphonoethyl | —N(morpholino) | —N(morpholino) |
| 89 | ethylthiomethyl | —N(morpholino) | —N(morpholino) |
| 90 | p-acetamidophenyl | —N(CH$_3$)$_2$ | —N(CH$_3$)$_2$ |
| 91 | p-nitrophenyl | —N(CH$_3$)$_2$ | —N(CH$_3$)$_2$ |
| 92 | benzyl | —N(CH$_3$)$_2$ | —N(CH$_3$)$_2$ |
| 93 | 2-nitroethyl | —NH—C$_6$H$_4$—Cl | —NH—C$_6$H$_4$—Cl |

The 2-sulfonyloxyethyl-phosphonic acids or 2-sulfonyloxyethyl-thionophosphonic acids used in this invention can be easily prepared from 2-sulfonyloxyethyl-phosphonic acid diesters of the following formula

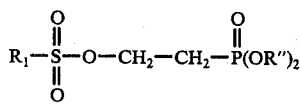

wherein $R_1$ is the same as defined above, and $R''$ is an alkyl group preferably having 1 to 4 carbon atoms, such as methyl, ethyl or isopropyl, a haloalkyl group preferably containing 1 to 4 carbon atoms, such as chloromethyl or 2-chloroethyl, or an alkenyl group containing 1 to 5 carbon atoms, such as an allyl group, which are prepared by reacting known 2-hydroxyethylphosphonic acid diesters (for their synthesis, see, for example, Organic Reactions, 1951, Vol. 6, page 290) with corresponding sulfonyl halides.

The compounds of formula (2) are neither described in the literature, but can be obtained by a method similar to general known reactions for synthesizing sulfonic esters from alcohols. For example, they can be obtained by mixing 2-hydroxyethylphosphonic acid diesters with the corresponding sulfonyl halides under cooling in the presence of a base, for example, inorganic alkalies such as sodium carbonate, sodium hydroxide, potassium hydroxide or calcium hydroxide, and organic amines such as triethyl amine, trimethylamine, pyridine or lutidine. Usually, the reaction temperature is about −20 to about 40° C. and the reaction time is about 30 minutes to about 40 hours.

Some embodiments of synthesizing active compounds of formula (1) from sulfonyloxyethylphosphonic acid diesters of formula (2) will be described below.

(1) Synthesis of compounds of formula (1-a)

These compounds of formula (1-a) are prepared by reacting phosphonic acid diesters of formula (2) with phosphorus pentachloride to form compounds of the following formula

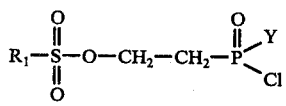

wherein $R_1$ is the same as defined above, and Y is Cl or —OR'' in which R'' is the same as defined above, that is, compounds of the following formula (3) or (4)

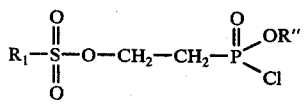

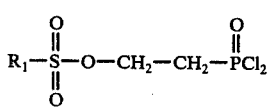

wherein $R_1$ and $R''$ are the same as defined above, and reacting the resulting phosphonochloridates or phosphonic acid dichlorides of formula (3) or (4) with water, alcohols or phenols of the formula

R'OH                                                         (5)

wherein R' is the same as defined above.

The reaction between the compound of formula (2) and phosphorus pentachloride can be carried out in the presence or absence of a solvent. Generally, it can be carried out at a temperature of about 0° C. to about 180° C., preferably room temperature to about 150° C. for a period of about 1 minute to about 5 hours, generally about 1 minute to about 2 hours, for example. Examples of the solvent that can be used in this reaction include halogenated hydrocarbons such as methylene chloride, chloroform or carbon tetrachloride, aromatic hydrocarbons such as toluene, benzene and xylene, and ethers such as diethyl ether or ethylene glycol dimethyl ether.

Preferably, the reaction of the compound of formula (3) or (4) with the compound of formula (5) is carried out in the presence of a solvent. The reaction proceeds more easily in the further presence of a basic compound. Thus, the reaction is preferably performed in the presence of a basic compound, for example, an inorganic alkali such as sodium hydroxide, potassium hydroxide or sodium carbonate, or an organic amine such as triethylamine, trimethylamine, lutidine or pyridine. The solvent may be the same as those exemplified with regard to the reaction of the compound of formula (2) with phosphorus pentachloride. Preferably, the reaction is carried out at a temperature of about −50° C. to about +100° C, preferably about −10° C. to about +25° C. The preferred reaction time is about 10 minutes to about 20 hours.

Compounds of formula (1-a) in which R' is hydrogen can be obtained also by other methods. For example, they can be easily obtained by reacting the phosphonic acid diesters of formula (2) with trialkylsilyl chlorides, for example, trimethylsilyl chloride, to form bistrimethylsilyl phosphonates of the following formula

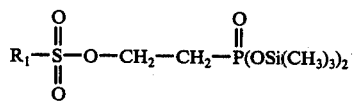

wherein $R_1$ is the same as defined above, and reacting the resulting compounds with water and/or lower alcohols with 1 to 4 carbon atoms such as methanol, ethanol or propanol. Usually, this reaction is carried out in he absence of a solvent. If desired, however, the same solvent as exemplified with regard to the reaction between the compound of formula (2) and phosphorus pentachloride can be used in this reaction, too. The reaction temperature is about −10° C. to about +70° C., preferably about 25 to about 40° C.

2. Synthesis of Compounds of Formula (1-b)

These compounds of formula (1-b) can be obtained by reacting the phosphonic acid dichlorides of formula (4) with phosphorus pentasulfide to form thionophosphonic acid dichlorides of the following formula

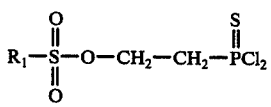

wherein $R_1$ is the same as defined above, and reacting the resulting compounds with water, alcohols or phenols of formula (5) or thiols of formula (7)

R'OH                                                         (5)

wherein R' is the same as defined above,

R'SH                                                         (7)

wherein R' is the same as defined above.

Usually, the reaction of the phosphonic acid dichlorides of formula (4) with phosphorus pentasulfide is carried out in the absence of a solvent. If desired, however, it can also be carried out in the presence of a solvent, for example, an aromatic hydrocarbon such as toluene, xylene or cumene. Preferably, the reaction is carried out at a temperature of about 50° C. to about 200° C., especially about 120° C. to about 150° C. The reaction time is, for example, about 1 minute to about 15 hours, preferably about 5 minutes to about 2 hours.

The reaction of the resulting thionophosphonic acid dichlorides of formula (6) with the compounds of formula (5) or (7) can be performed, for example, for about 1 minute to about 50 hours at a temperature of preferably about −20° C. to about +150° C., more preferably about 0° C. to about 40° C. Since the reaction proceeds more easily in the presence of a basic compound, it is preferred to carry it out in the presence of a basic compound, for example, an inorganic alkali such as sodium carbonate, sodium hydroxide, potassium hydroxide, or calcium carbonate, or an organic amine such as triethylamine, trimethylamine, pyridine or lutidine. The reaction can be performed in the presence or absence of a solvent. Specific examples of the solvent are the same as those exemplified with regard to the reaction of the compounds of formula (2) with phosphorous pentachloride.

3. Synthesis of compounds of formula (1—c):-

Of the compounds of formula (1—c), those of the following formula

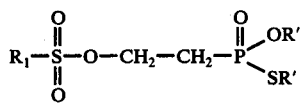 (1-c-A)

wherein $R_1$ and R' are the same as defined above, can by synthesized by reacting the phosphonochloridates of formula (3) with the thiols of formula (7) in the presence of basic compounds, or by reacting the phosphonic acid dichlorides of formula (4) with the thiols of formula (7) and the water, alcohols or phenols of formula (5) in the presence of bases. The basic compounds may be the same as the inorganic alkalies and organic amines exemplified above. The reaction temperature is preferably about −50 to about +100° C., especially about −20° to about +25° C. The reaction solvent and the reaction time may be the same as those described with regard to the reaction between the thionophosphonic acid dichlorides of formula (6) and the compounds of formula (7).

Of the compounds of formula (1—c), those having the following formula (1—c—B)

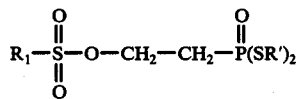 (1-c-B)

wherein $R_1$ and R' are the same as defined above, can be synthesized by reacting the phosphonic acid dichlorides of formula (4) with the thiols of formula (7) under the same conditions as described with respect to the preparation of the compounds of formula (1-c-A).

Of the compounds of formula (1-c), those having the following formula (1-c-C)

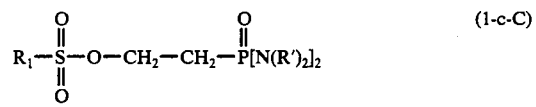 (1-c-C)

wherein $R_1$ and R' are the same as defined above, can be synthesized by reacting the phosphonoyl dichlorides of formula (4) with compounds of formula (8)

wherein R' is the same as defined above and can represent a morpholino group including N, which are primary or secondary amines, in the presence of basic compounds. Examples of the basic compounds are the same as those given hereinabove. The reaction conditions can be the same as those described with regard to the preparation of the compounds of formula (1-c-A).

The plant growth regulator composition of this invention usually consists of a growth regulating amount of the active compound of formula (1) and a gaseous, liquid or solid diluent, and can be used in any required formulation such as a wettable powder, emulsifiable concentrate, liquid preparation or paste. The amount of the active compound of formula (1) can be varied over a wide range of about 0.00001 to about 99% by weight, preferably 0.001 - 50%, and more preferably 0.005 - 10%, based on the weight of the plant growth regulator composition. Examples of such a diluent include liquid diluents such as water, methyl alcohol, ethyl alcohol, isopropyl alcohol, acetone, methyl ethyl ketone, methyl cellosolve, diethylene glycol monoethyl ether, dimethyl sulfoxide, dimethyl formamide, isopropyl acetate, kerosene, benzene, toluene, or petroleum ether, gaseous diluents such as air, nitrogen, argon, propane, ethane or vinyl chloride, and solid diluents such as talc, diatomaceous earth, kaolinite, montmorillonite, attapulgite, wheat flour, and soybean flour.

According to this invention, there is provided a method for regulating the growth of plants, which comprises applying the compound of formula (1) to one or more parts of a plant, such as a stem, leaf, trunk, branch, fruit, seed, root or bud or to the locus in which the plant is growing or will be grown; or treating one or more part of a plant with the compound of formula (1).

The amount of the compound of formula (1) to be applied can be properly chosen according to the plant to be treated, the time of application, the intended regulating action, etc. Usually, the amount is about 10 to 4000 g, preferably about 20 to 2000 g, per 10 ares of the locus in which the plant is growing or will be grown. When the compound is to be applied to a plant itself, for example, when it is applied to fruits or rubber trees, the amount is varied according to the surface area of the plant or the type of the compound of formula (1). Usually, a liquid composition containing the compound of formula (1) in a concentration of about 10 to 10,000 ppm is applied in an amount of about 2 to 100 ml. When the compound of formula (1) is applied by immersing one or more parts of a plant, for example, seeds, roots such as bulbs or seed potatoes, and buds in it, the intended regulating effect can be obtained by immersing them in a liquid composition containing the compound in a concentration of about 10 to 10,000 ppm for about 3 minutes to about 6 hours.

The active compound used in this invention is not limited to one species, but two or more kinds of the compound can be used in mixture. The plant growth regulator of this invention can also be used with fertilizers, insecticides, fungicides, herbicides and other plant growth regulators.

The following Examples illustrate the present invention.

Examples of Preparation of the Active Compounds

Example 1

3.9 g of dimethyl 2-hydroxyethylphosphonate and 5.9 g of pyridine were dissolved in 40 ml. of dry diethyl ether, and the solution was cooled with ice to −5° C. A solution of 6.0 g of γ-bromopropylsulfonyl chloride in 30 ml. of dry diethyl ether was added dropwise to the cooled solution by means of a dropping funnel. After the addition, the mixed solution was allowed to stand for 24 hours at 0° to 5° C. The reaction mixture was poured into 50 ml. of 5% hydrochloric acid, and extracted with diethyl ether. The extract was dried over anhydrous sodium sulfate, and the solvent was distilled off at reduced pressure. The product was further dried at room temperature at 0.7 mmHg for 18 hours to afford dimethyl 2-(3-bromopropylsulfonyloxy)ethylphosphonate as a colorless oil in a yield of 75 mol %. The product showed the following characteristic values.

$n_D^{22} = 1.4960$

Nuclear magnetic resonance spectrum (CDCl$_3$)

$\delta = 2.30$ ppm (dt, 2H), 2.00 – 2.60 (m, 2H), 3.36 – 3.70 (m, 4H), 3.77 (d, 6H), 4.38 (dt, 2H)

2.0 g of the dimethyl-2-(3-bromopropylsulfonyloxy)ethylphosphonate was dissolved in 30 ml. of dry methylene chloride. 2.5 g. of phosphorus pentachloride was added, and the mixture was refluxed for one hour. The solvent was distilled off at reduced pressure, and dry sulfur dioxide was passed into the residue, and the by products were distilled off under reduced pressure. 10 ml. of methylene chloride was added to form a solution, and water (1 ml) was added with ice cooling. The mixture was stirred for 20 minutes at room temperature, and the solvent was distilled off at reduced pressure. 20 ml. of acetone was added to form a solution. Activated carbon was added in a small amount to decolorize the solution and remove the remaining hydrogen chloride. The activated carbon was separated by filtration, and the solvent was disstilled off at reduced pressure. The residue was dried in vacuo to afford a colorless oil identified as Compound No. 1 which comes within the formula (1-a) given hereinabove. The yield was 83 mol%. The compound had the following characteristic value.

$n_D^{23.5° C} = 1.4935$

By the same procedure as above, Compounds Nos. 2 to 4, 6 and 10 to 16, 18, 19, 31 to 33, 35 to 37 and 41 of formula (1-a) were prepared.

The characteristic values are as follows:

| No. 3 | $N_D^{23.5° C} = 1.4800$ |
| 4 | $N_D^{23.5° C} = 1.4712$ |
| 6 | $N_D^{23.5° C} = 1.4673$ |
| 10 | $N_D^{23.5° C} = 1.4745$ |
| 11 | $N_D^{23.5° C} = 1.5149$ |
| 14 | $N_D^{23.5° C} = 1.5040$ |
| 16 | m.p = 110 to 113° C. |
| 41 | $n_D^{20° C} = 1.4609$ |

Example 2

2.0 g of dimethyl 2-(2-methoxycarbonylethylsulfonyloxy)ethylphosphonate was placed in a reactor purged with dry nitrogen, and with stirring at 140° C., 4.8 g of phosphorus pentachloride was added. After reacting them for 10 minutes, the reaction mixture was cooled to room temperature. Dry sulfur dioxide gas was passed into the mixture, and the by-products were distilled off at reduced pressure. 10 ml. of methylene chloride was added to form a solution, and then 1.25 g (equivalent) of dodecyl alcohol was added dropwise. The mixture was further cooled to −10° C., and 0.53 g of pyridine was added dropwise with stirring. After allowing the mixture to sgand for one day, the resulting crystals were separated by filtration at reduced pressure. With cooling, water in an amount exceeding the equivalent weight was added to the mother liquor. The mixture was stirred at room temperature for 2 hours, and the solvent was distilled off at reduced pressure. 10 ml. of water was added to the residue to form a solution. Then, activated carbon was added to decolorize the solution, followed by filtration. The mother liquor was concentrated at reduced pressure, and dried in vacuo to form a colorless liquid identified as Compound No. 26 of formula (1-a). The yield was 30 mol %. The compound showed the following characteristic values.

IR spectrum: 3400 cm$^{-1}$, 2260, 1700, 1350, 1160, 1040, 950

By the same procedure as above, Compounds Nos. 25, 27, 28, 29, and 30 were obtained.

Example 3

60 g of diethyl 2-hydroxyethylphosphonate and 4.2 g of triethylamine were dissolved in 75 ml. of dry diethyl ether, and the solution was cooled to −5° C.

4.45 g of methanesulfonyl chloride was dissolved in 75 ml of dry diethyl ether, and the solution was added dropwise with stirring to the above cooled solution by means of a dropping funnel equipped with a side tube. After the addition, the temperature of the solution was returned to room temperature, and the solution was stirred for an additional 5 hours. The reaction mixture was concentrated at reduced pressure, and again diethyl ether was added. The insoluble matter was separated by filtration. The ethereal phase was washed with water, and dried, and the solvent was distilled off. The residue was dried at 0.7 mmHg at room temperature to afford a colorless oily substance. Thus,

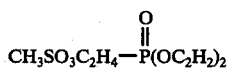

was obtained in a yield of 80 mol%. The product was clearly characterized by the following spectra.

IR spectrum: 1250 cm$^{-1}$ (characteristic absorption of P=O); 1030 cm$^{-1}$, 960 cm$^{-1}$ (characteristic absorption of P-O-C); 1360 cm$^{-1}$, 1175 cm$^{-1}$ (—O-SO$_2$- characteristic absorption);

NMR spectrum (solvent, CD$_3$OD/CDCl$_3$=1/7 volume ratio): $\delta = 1.34$ ppm (t, 6H), 2.30 (dt, 2H), 3.05 (s, 3H), 4.14 (dq, 4H), 4.45 (dt, 2H).

Mass spectrum: P (parent peak) = 260.

A two-necked flask purged with dry argon was charged with 2.14 g of diethyl 2-methanesulfonyloxyethylphosphonate and 3.38 g of phosphorus pentachloride, and with stirring, they were heated to 110° C. Then, the temperature was raised to 150° C., and the mixture was maintained at this temperature for 20 minutes. The reaction mixture was then cooled to room temperature, and dry sulfur dioxide gas was passed into the mixture to oxidize the unreacted phosphorus pentachloride. The by-products were distilled off at reduced pressure, and 20 ml. of diethyl ether was added to dissolve the resulting product. Water in an amount exceeding the equivalent weight was added dropwise to the resulting solution with stirring. The solvent was distilled off at reduced pressure, and the residue was dried at 0.7 mmHg at room temperature to afford white crystals. The crystals were recrystallized from a solvent consisting of chloroform and acetone in a 1:1 volume ratio. Compound No. 38 was obtained as colorless crystals having a melting point of 116.5 to 117° C. in a yield of 67 mol %.

The product was clearly characterized by the following spectra.

IR spectrum: 2280 cm$^{-1}$,

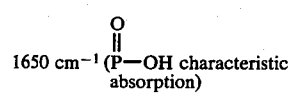

1650 cm$^{-1}$ (P—OH characteristic absorption)

1020 cm$^{-1}$, 970 cm$^{-1}$ (P-O characteristic absorption)

1350 cm$^{-1}$, 1140 cm$^{-1}$ (-O-SO$_2$- characteristic absorption)

NMR spectrum (solvent, CD$_3$OC/CDCl$_3$ = 1/7 volume ratio): δ = 2.26 ppm (dt, 2H), 3.10 (s, 3H), 4.44 (dt, 2H), 5.36 (s, 2H) Elemental analysis:

|  | C | H | O | P | S |
|---|---|---|---|---|---|
| Calculated (%): | 17.65 | 4.44 | 47.03 | 15.17 | 15.71 |
| Found (%): | 18.18 | 4.39 | 46.98 | 15.20 | 15.50 |

By the same procedure as above, Compounds Nos. 40, 42, 43, 45 and 46 of formula (1-a) were prepared. The characteristic values of these compounds were as follows:

| Compounds Nos. | Properties |
|---|---|
| 40 | m.p. = 88 to 89° C. |
| 43 | m.p. = 131 to 132° C. |
| 45 | m.p. = 122 to 123.5° C. |
| 46 | m.p. = 143 to 146° C. |
| 42 | NMR spectrum (CD$_3$QD/CDCl$_3$ = 1/7): δ = 2.20 ppm (dt, 2H), 4.30 (dt, 2H), 5.86(s, 2H), 7.27 to 8.05 (m, 5H) |

Example 4

2.6 g of dimethyl 2-(3-ethoxypropylsulfonyloxy) ethylphosphonate was placed in a reactor purged with dry nitrogen, and with stirring at 140° C., 4.5 g of phosphorus pentachloride was added. After reacting for 10 minutes, the reaction mixture was cooled to room temperature, and a gas of dry sulfur dioxide was passed into the mixture. The resulting by-products were distilled off at reduced pressure. The residual oil was dissolved in 10 ml. of methylene chloride, and then water (1 ml.) was added with ice cooling. The mixture was stirred at room temperature for 20 minutes, and the solvent was distilled off at reduced pressure. 10 ml. of water was added to form a solution, and activated carbon was added in a small amount to decolorize the solution and remove the remaining hydrogen chloride. The activated carbon was separated by filtration, and the solvent was distilled off at reduced pressure. The product was further dried in vacuo to afford a colorless oil identified as Compound No. 7 of formula (1-a) in a yield of 62 mol%. This compound exhibited a refractive index (n$_D^{23.5°}$ C) of 1.4805.

By the same procedure as above, Compounds Nos. 8, 9, 17, and 20 to 24 of formula (1-a) were prepared.

The characteristic values of these compounds were as follows:

| Compounds Nos. | Properties |
|---|---|
| 8 | m.p. = 145 to 148° C. |
| 17 | m.p. = 111 to 117° C. |
| 24 | m.p. = 114.5 to 120° C. |

Example 5

3.0 g of diethyl 2-methanesulfonyloxyethylphosphonate obtained in the same way as in Example 3 and 2.4 g of phosphorus pentachloride were dissolved in 20 ml. of dry toluene, and the solution was heated under reflux for 2.5 hours at atmospheric pressure. Then, dry sulfur dioxide was passed into the reaction mixture to oxidize the unreacted phosphorus pentachloride. The solvent and by-products were distilled off at reduced pressure. To the resulting oily substance, 20 ml. of diethyl ether was added. Water in an amount exceeding the equivalent weight was added to the solution with stirring. The solvent was distilled off at reduced pressure, and the residue was dried at 0.7 mmHg and at room temperature to afford a colorless oil which was identified as Compound No. 39. The yield was 97 mol%. The product was clearly characterized by the following spectra.

IR spectrum

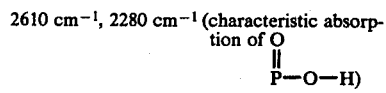

2610 cm$^{-1}$, 2280 cm$^{-1}$ (characteristic absorption of O‖P—O—H)

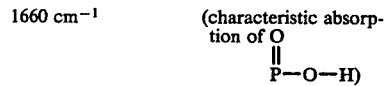

1660 cm$^{-1}$ (characteristic absorption of O‖P—O—H)

950 to 1040 cm$^{-1}$ (P-O characteristic absorption)

1360 cm$^{-1}$, 1180 cm$^{-1}$ (—O-SO$_2$- characteristic absorption)

NMR spectrum (solvent, CD$_3$OD/CDCl$_3$ = 1/7 volume ratio) δ = 1.35 ppm (t, 3H), 2.30 (dt, 2H), 3.09 (s, 3H), 4.11 (dq, 2H), 4.47 (dt, 2H), 5.84 (s, 1H)

Mass spectrum: P=232

By the same procedure as above, Compound No. 44 of formula (1-a) was prepared. The IR spectrum of this compound was as follows:

2980 cm$^{-1}$, 2280, 1595, 1360, 1190, 1175, 1040 to 1000, 950.

Example 6

Dimethyl 2-vinylsulfonyloxyethylphosphonate was prepared in the same way as in Example 1 from 3.8 g of dimethyl 2-hydroxyethylphosphonate, 1.9 g of pyridine and 4.0 g of 2-chloroethylsulfonyl chloride. The yield was 20 mol%. The NMR spectrum (CDCl₃) of this product was as follows:

δ=2.30 ppm (dt, 2H), 3.78 (d, 6H), 4.32 (dt, 2H), 6.1 to 6.6 (m, 3H).

Compound No. 34 of formula (1-a) was prepared in the same way as in Example 1 from 2.44 g of dimethyl 2-vinylsulfonyloxyethylphosphonate and 2.10 g of phosphorus pentachloride. The yield was 60 mol%. This product showed the following nuclear magnetic resonance spectrum.

δ(CD₃OD) = 6.8 to 6.1 ppm (m, 3H), 5.1 ppm (s, H), 4.4 (dt, 2H), 3.72 (d, 3H), 2.28 (dt, 2H)

Compounds Nos. 35, 36 and 37 of formula (1-a) were prepared in the same way as above.

Example 7

By the same procedure as in Example 3, dimethyl 2-methanesulfonyloxyethylphosphonate was prepared from 15.4 g of dimethyl 2-hydroxyethylphosphonate, 39.5 g of pyridine and 11.5 g of methanesulfonyl chloride in a yield of 88 mol%.

Nuclear magnetic resonance spectrum (CDCl₃)

δ=2.31 ppm (dt, 2H), 3.09 (s, 3H), 3.80 (d, 6H), 4.47 (dt, 2H)

13.9 g of the dimethyl 2-methanesulfonyloxyethylphosphonate was placed in a reactor and heated to 140° to 150° C. With stirring, 30.0 g of phosphorus pentachloride was added, and the reaction was performed for 20 minutes. The reaction mixture was cooled to room temperature, and a dry sulfurous acid gas was passed into the reaction mixture to oxidize the unreacted phosphorus pentachloride. The resulting by-products were distilled off at reduced pressure, and to the remaining oily liquid, 3.4 g of phosphorus pentasulfide was added. The mixture was heated to 120 to 130° C. for 2 hours, and extracted with 100 ml. of dry diethyl ether. The insoluble matter was separated by filtration, and the filtrate was concentrated at reduced pressure. The concentrate was dried in vacuo (0.1 mmHg) to afford 6.2 g of a brown oil in a yield of 41.2 mol%. This compound showed the following characteristic values, and was identified as Compound No. 47 of formula (1-b).

Infrared absorption spectrum (cm⁻¹)

3040, 2980, 2940, 1465, 1360, 1240, 1180, 1050, 990, 960, 880, 800, 760, 720.

Nuclear magnetic resonance spectrum (CDCl₃)

δ=3.15 ppm (s, 3H), 3.37 (dt, 2H), 4.75 (dt, 2H)

Refractive index $n_D^{25} = 1.4650$

By the same procedure as above, Compound No. 48 of formula (1-b) was prepared. This product has a refractive index ($n_D^{25°C}$) of 1.5536.

Example 8

2.2 g of the 2-methanesulfonyloxyethylthionophosphonyl dichloride obtained in Example 7 was cooled with ice, and with stirring, 2.0 g of water was added dropwise. After the addition, the mixture was warmed to 40° C., reacted for one hour, and concentrated at reduced pressure at room temperature. The residue was dissolved in a small amount of water, and a small amount of activated carbon was added. The mixture was stirred, and filtered. The mother liquor was concentrated at reduced pressure, and dried in vacuo (0.1 mmHg) to afford 1.4 g of a highly viscous liquid identified as Compound No. 49 of formula (1-b).

The product showed the following characteristic values, and was identified as Compound No. 49.

Infrared absorption spectrum (cm⁻¹)

3020, 2930, 2600, 2290, 2160, 1630, 1350, 1250, 1170, 1040-920, 790, 730.

Nuclear magnetic resonance spectrum (CD₃OD)

δ=2.33 ppm (dt, 2H), 3.11 (s, 3H), 4.45 (dt, 2H), 5.47 (s, 2H)

Refractive index $n_D^{25} = 1.5075$

By the same procedure as above, Compounds Nos. 50 and 52 of formula (1-b) were prepared. Compound No. 52 had a retractive index ($n_D^{25°}$C) of 1.5450.

Example 9

2.2 g of 2-methanesulfonyloxyethylthionosphonic acid dichloride obtained in Example 7 was dissolved in 20 ml. of dry diethyl ether, and with stirring, 1.8 g of benzyl alcohol was added dropwise. Then, 0.8 g of pyridine was added dropwise with stirring under ice cooling. After the addition, the mixture was allowed to stand at room temperature for one weak, and the resulting crystals were separated by filtration. The mother liquor was concentrated at reduced pressure, and dried in vacuo to afford 1.6 g of a viscous liquid identified as Compound No. 51 of formula (1-b).

By the same procedure as above, Compounds Nos. 53 to 56 of formula (1-b) were prepared.

Example 10

7.8 g of dimethyl 2-methanesulfonyloxyethyl-phosphonate was placed in a reactor, and heated to 140 to 150° C. With stirring, 16.8 g of phosphorus pentachloride was added, and the reaction was carried out for 20 minutes. The reaction mixture was cooled to room temperature, and a dry sulfurous acid gas was passed into the mixture to oxidize the unreacted phosphorus pentachloride. The resulting by-products were distilled off at reduced pressure. The residual oily liquid was dissolved in 60 ml. of dry methylene chloride, and the solution was cooled to −10 to −18° C. 21.3 g of p-chlorobenzenethiol and 11.1 g of pyridine were simultaneously added dropwise to this solution with stirring. After the addition, the solution was allowed to stand at 0 to 5° C. for 48 hours. The resulting crystals were separated by filtration, and the mother liquor was concentrated at reduced pressure to give a residual solid. 100 ml. of diethyl ether was added to the solid to extract a soluble matter. The ethereal phase was then concentrated at reduced pressure. The resulting solid was recrystallized from petroleum ether to afford colorless acicular crystals identified as Compound No. 57 of formula (1-c) in a yield of 30 mol%. This product had the following characteristic values.

Infrared absorption spectrum (cm⁻¹)

3040, 2960, 1595, 1490, 1410, 1338, 1180,
1165, 1100, 1040, 1020, 990, 960, 850, 720

Nuclear magnetic resonance spectrum (CDCl₃)

δ=2.50 ppm (dt, 2H), 3.02 (s, 3H), 4.15 (d, 4H), 4.40 (dt, 2H), 7.32 (s, 10H)

Melting point 84 to 85.5° C.

By the same procedure as above, Compounds Nos. 58, 59, 60, 61, 62, 63 and 71 of formula (1-c) were prepared. Compound No. 58 had a melting point of 56 to 59° C., and Compound No. 60 had a refractive index ($n_D^{25°}$ C) of 1.6200.

Example 11

Compound No. 64 of formula (1-c) was prepared by the same procedure as in Example 7 from 7.6 g of dimethyl 2-methanesulfonyloxyethylphosphonate, 9.0 g of phosphorus pentachloride and 6.2 g of ethyl thiol. The yield was 48 mol%. This product showed the following characteristic values.

Infrared absorption spectrum (cm⁻¹)

3020, 2970, 2940, 1460, 1350, 1270, 1170, 1135, 1040, 940, 880, 810, 720

By the same procedure as above, Compounds Nos. 65 and 72 of formula (1-c) were prepared.

Example 12

Compound No. 68 of formula (1-c) was prepared in the same way as in Example 1 from 2.3 g of dimethyl 2-methanesulfonyloxyethylphosphonate, 2.3 g of phosphorus pentachloride and 0.46 g of dimethylamine. The yield was 52 mol%. The IR spectrum of this product was as follows:

2980 cm⁻¹, 1360, 1250, 1180, 1030, 960-950

By the same procedure as above, Compound No. 69 of formula (1-c) was prepared.

Example 13

Compound No. 66 of formula (1-c) was prepared in the same way as in Example 1 from 1.3 g of dimethyl 2-(p-chlorobenzenesulfonyloxy(ethylphosphonate, 4.6 g of phosphorus pentachloride, 1.2 g of benzyl thiol and 0.2 g of water. By the same procedure as above, Compounds Nos. 67 and 70 of formula (1-c) were obtained.

Example 14

7.1 g of diethyl 2-methanesulfonyloxyethylphosphonate was heated to 145° C. With stirring, 14.2 g of phosphorus pentachloride was added, and they were reacted for 30 minutes. The mixture was cooled to room temperature. Sulfur dioxide gas was passed into the mixture, and the by-products were distilled at reduced pressure. 50 ml. of dry methylene dichloride was added to the residue to form a solution. The solution was cooled to −20° C., and 7.5 ml. of dry dimethylamine was passed into the solution. After allowing the solution to stand for 48 hours, the solvent was distilled at reduced pressure. Then, 50 ml. of dry ether was added, and the insoluble matter was filtered. The mother liquor was concentrated at reduced pressure, and dried in vacuo (0.7 mmHg) at room temperature to afford an oily liquid which was identified as Compound No. 73 from the following characteristic values.

Infrared absorption spectrum: 2940 cm⁻¹, 1460, 1360, 1310, 1265, 1175, 990, 725 Refractive index ($n_D^{13°}$ C): 1.4623

Example 15

7.1 g of diethyl 2-diethyl 2-methanesulfonyloxyethylphosphonate was heated to 145° C., and with stirring, 14.2 g of phosphorus pentachloride was added. The mixture was reacted for 30 minutes, and then cooled to room temperature. Sulfur dioxide gas was passed into the mixture, and the by-products were distilled off at reduced pressure. 50 ml. of dry methylene dichloride was added to the residue to form a solution. The solution was cooled to −20° C., and a solution of 11.3 g of aniline in 20 ml. of methylene dichloride was added dropwise. At 50° C., the mixture was allowed to stand for 48 hours. The resulting precipitate was separated by filtration. The mother liquor was concentrated at reduced pressure, and dried in vacuo (0.7 mmHg) at room temperature to afford a waxy substance. This product was identified as Compound No. 74 from its infrared absorption spectrum.

Infrared absorption spectrum:
3040 − 2900 cm⁻¹, 1590, 1495, 1350,
1180 − 1120, 1020 − 930, 750, 690

EXAMPLE 16

6.9 g of dimethyl 2-methanesulfonyloxyethylphosphonate was heated to 145° C., and with stirring 14.8 g of phosphorus pentachloride was added. They were reacted for 20 minutes. The reaction mixture was cooled to room temperature, and then sulfur dioxide was passed into the mixture. The by-products were distilled at reduced pressure. 50 ml. of methylene dichloride was added to the resulting residue to form a solution. 7.7 g of isopropylamine was added to the resulting methylene dichloride solution with cooling, and the mixture was allowed to stand at 5° C. for 48 hours. The resjlting precipitate was separated by filtration, concentrated at reduced pressure, and dried in vacuo to afford an oily liquid. This product was identified as Compound No. 75 from its infrared absorption spectrum and refractive index.

Infrared absorption spectrum:
3190 cm⁻¹, 2970, 1370, 1300, 1210, 1170,
1130, 1040, 930

Refractive index ($n_D^{17°}$ C):
1.4768

Example 17

A solid product was prepared in the same way as in Example 16 from 5.9 g of dimethyl 2-methanesulfonyloxyethylphosphonate, 18.7 g of phosphorus pentachloride and 14.3 g of p-chloroaniline. This product was identified as compound No. 76 from its infrared absorption spectrum.

Infrared absorption spectrum:
2940 cm⁻¹, 1490, 1350, 1280, 1222, 1168,
1090, 940, 810

Example 18

A viscous liquid was prepared in the same way as in Example 16 from 7.5 g of dimethyl 2-(p-toluenesulfonyl) oxyethylphosphonate, 12.2 g of phosphorus pentachloride and 8.6 g of isopropylamine. This product was identified as Compound No. 81 from its infrared absorption spectrum and refractive index.

Infrared absorption spectrum:
3240 cm⁻¹, 2970, 1595, 1460, 1360, 1300,
1170-1218, 1120, 1050, 1070, 815, 680
Refractive index ($n_D^{17°}$ C): 1.5027

By the same procedure as above, Compounds Nos. 77 to 80, and 82 to 93 of formula (1-c) were prepared.

Examples of Formulation and Application (all parts are by weight)

Example 1 (liquid preparation)

A liquid preparation with an active ingredient concentration of 30% was prepared by mixing the following ingredients.

| | |
|---|---|
| 2-Methanesulfonyloxyethylthionophosphonate (Compound No. 49 of formula (1-b) | 30 parts |
| Ethanol | 30 parts |
| Propylene glycol | 10 parts |
| Water | 25 parts |
| Polyoxyethylene dodecyl ether | 5 parts |

In use, the liquid preparation was diluted with water to the desired concentration, and sprayed.

Example 2 (liquid preparation)

A liquid preparation with an active ingredient concentration of 30% was prepared by uniformly mixing the following ingredients.

| | |
|---|---|
| 2-(2-carboxyethylsulfonyloxy)ethylphosphonic acid (Compound No. 8 of formula (1-a) | 30 parts |
| Propylene glycol | 25 parts |
| Ethyl alcohol | 30 parts |
| Water | 10 parts |
| Alkylbenzenesulfonate as surfactant (NEOGEN, a registered trademark of Daiichi Kogyo Seiyaku K.K.) | 5 parts |

In use, the liquid preparation was diluted with water to the desired concentration, and sprayed.

Example 3 (emulsifiable concentrate)

An emulsifiable concentrate with an active ingredient concentration of 40% was prepared by mixing the following ingredients.

| | |
|---|---|
| Dithio ester of S,S-diphenyl-2-2-methanesulfonyloxyethylphosphonic acid (Compound No. 58 of formula (1-c)) | 40 parts |
| Xylol | 50 parts |
| Sorpol 800 (trademark for polyoxyethylene surfactant, made by Toho Chemical Co., Ltd.) | 10 parts |

In use, the emulsifiable concentrate was diluted with water to the desired concentration, and sprayed.

Example 4 (emulsifiable concentrate)

An emulsifiable concentrate with an active ingredient concentration of 50% was prepared by uniformly mixing the following ingredients.

| | |
|---|---|
| Monoethyl 2-(3-thiocyanatopropylsulfonyloxy)ethylphosphonate (Compound No. 14 of formula (1-a)) | 50 parts |
| Xylol | 40 parts |
| Sorpol 800 | 10 parts |

In use, the emulsifiable concentrate was diluted with water to the desired concentration, and sprayed.

Example 5 (wettable powder)

A wettable powder with an active ingredient concentration of 30% was prepared by mixing and pulverizing the following ingredients.

| | |
|---|---|
| 2-(2-Carboxyethylethylsulfonyloxy)ethylthionophosphonic acid (Compound No. 50 of formula (1-b)) | 30 parts |
| Mixture of equal amounts of talc and clay | 65 parts |
| Sodium alkylbenzenesulfonate | 3 parts |
| Sodium dinaphthylmethanedisulfonate | 2 parts |

In use, the wettable powder was diluted with water to the desired concentration.

Example 6 (wettable powder)

A wettable powder having an active ingredient concentration of 40% was prepared by mixing and pulverizing the following ingredients.

| | |
|---|---|
| 2-(2-Phthalimidoethylsulfonyloxy)ethylphosphonic acid (Compound No. 17 of formula (1-a)) | 40 parts |
| Mixture of equal amounts of Zieklite and Kunilite (trademarks for fillers) | 55 parts |
| Sodium alkylbenzenesulfonate as surfactant | 3 parts |
| Sodium dinaphthylmethanedisulfonate | 2 parts |

In use, the wettable powder was diluted with water to the desired concentration.

Example 7 (paste)

A paste having an active ingredient concentration of 3% was prepared by mixing the following ingredients thoroughly.

| | |
|---|---|
| Monomethyl 2-(3-bromopropylsulfonyloxy)ethylsulfonate (Compound No. 1 of formula (1-a) | 3 parts |
| Sorbitol | 20 parts |
| Sorbitan-long-chain fatty acid ester | 10 parts |
| Nineral oil | 10 parts |
| Water | 57 parts |

In use, the paste was applied in the desired amount.

Example 8 (emulsifiable concentrate

| | |
|---|---|
| Monoethyl 2-methanesulfonyloxyethylphosphonate | 50 parts |
| Xylol | 40 parts |
| Polyoxyethylene compound as a surfactant (Sorpol 800, a registered trademark of Toho Chemical Co., Ltd.) | 10 parts |

The above ingredients were uniformly mixed to form an emulsifiable concentrate having an active ingredient content of 50%.

In use, the emulsifiable concentrate was sprayed after being diluted with water to the desired concentration.

Example 9 (liquid preparation)

| | |
|---|---|
| 2-Methanesulfonyloxyethylphosphonic acid | 30 parts |
| Propylene glycol | 25 parts |
| Ethyl alcohol | 30 parts |

-continued

| | |
|---|---|
| Water | 10 parts |
| Alkylbenzenesulfonate as a surfactant (NEOGEN, a trademark of Daiichi Kogyo Seiyaku K.K.) | 5 parts |

These ingredients were mixed uniformly to form a liquid preparation having an active ingredient content of 30%. In use, it was diluted to the desired concentration, and sprayed.

Example 10 (wettable powder)

| | |
|---|---|
| 2-Methanesulfonyloxyethylphosphonic acid | 40 parts |
| Mixture of equal amount of Zieklite and Kunilite as fillers (a trademark, Kokuho Co., Ltd.) | 55 parts |
| Sorpol 800 (a trademark for a surface active agent) | 5 parts |

The above ingredients were mixed, and pulverized to form a wettable powder having an active ingredient content of 40%. In use, the wettable powder was diluted to the desired concentration, and sprayed.

Example 11 (liquid preparation)

| | |
|---|---|
| 2-Methanesulfonyloxyethylphosphonic acid bis(dimethylamide) | 30 parts |
| Ethyl alcohol | 30 parts |
| Propylene glycol | 25 parts |
| Water | 10 parts |
| Alkylbenzenesulfonate (NEOGEN, a registered trademark, Daiichi Kogyo Seiyaku K.K.) | 5 parts |

These ingredients were mixed uniformly to form a liquid preparation having an active ingredient content of 30%. In use, the liquid preparation was diluted to the desired concentration, and sprayed.

Example 12 (emulsifiable concentrate)

| | |
|---|---|
| 2-p-toluenesulfonyloxyethyl-phosphonic acid bis(isopropylamide) | 50 parts |
| Xylol | 40 parts |
| Sorpol 800 (a registered trademark for a polyoxyethylene as a surfactance, Toho Chemical Co., Ltd.) | 10 parts |

The above ingredients were uniformly mixed to form an emulsifiable concentrate having an active ingredient of 50%. In use, the emulsifiable concentrate was diluted with water to the desired concentration, and sprayed.

Example 13 (wettable powder)

| | |
|---|---|
| 2-Methanesulfonyloxyethylphosphonic acid bis(dimethylamide) | 40 parts |
| Mixture of equal amounts of Zieklite and Kunilite as fillers | 55 parts |
| Sorpol 800 (surfactant) | 5 parts |

The above ingredients were mixed and pulverized to form a wettable powder having an active ingredient content of 40%. In use, it was diluted to the desired concentration and sprayed.

Example 14 (paste)

| | |
|---|---|
| 2-Methanesulfonyloxyethylphosphonic acid bis(isopropylamide) | 2 parts |
| Bentonite | 25 parts |
| Starch | 33 parts |
| Vaseline | 20 parts |

The above ingredients were mixed well with water to form a paste having an active ingredient content of 2%.

Test Example 1

Test for swelling of young garden peas

Pots with an inside diameter of 9 cm were filled with a field soil of valcanic ashes. Fifteen seeds of garden pea were sown in each pot, and grown for one week in a constant temperature chamber (dark place) at 25° C. 2 ml. of the wettable powder of this invention diluted with water to each of the concentrations shown in Table 1 was sprayed uniformly over the upper ground of garden peas grown to a height of 5 to 7 cm. These plants were placed in a dark room at 25° C., and the extent of swelling of the stem of the peas was evaluated on the following scale. The results are shown in Table 1.

Table 1

(The results of the swelling test on garden peas)

| Concentration (ppm) | Compound No. 1 | No. 2 | No. 3 | No. 4 | No. 5 | No. 6 | No. 7 | No. 8 | No. 9 | No. 10 | No. 11 | No. 12 |
|---|---|---|---|---|---|---|---|---|---|---|---|---|
| 8,000 | +++ | +++ | +++ | +++ | ++ | ++ | +++ | +++ | +++ | ++ ~+++ | ++ | ++ |
| 4,000 | ++ | ++~+++ | ++~+++ | ++~ | ++ | ++ | ++~+++ | ++~+++ | ++ | ++ | ++ | + |
| 2,000 | + | + | + | + | + | + | ++ | ++ | ++ | + | + | + |
| 1,000 | + | + | + | + | ± | ± | + | + | + | + | + | ± |

| Concentration (ppm) | No. 13 | No. 14 | No. 15 | No. 16 | No. 17 | No. 18 | No. 19 | No. 20 | No. 21 | No. 22 | No. 23 | No. 24 |
|---|---|---|---|---|---|---|---|---|---|---|---|---|
| 8,000 | ++ | ++ | ++~+++ | ++ | ++ | ++ | +++ | ++ | +++ | +++ | ++ | ++ |
| 4,000 | + | + | ++ | + | ++ | + | ++ | + | ++ | ++ | + | + |
| 2,000 | ± | + | + | + | + | + | + | + | + | + | + | + |
| 1,000 | ± | ±~+ | ± | ± | + | ± | + | ± | + | + | ± | ± |

| Concentration (ppm) | No. 25 | No. 26 | No. 27 | No. 31 | No. 32 | No. 33 | No. 34 | No. 35 | No. 47 | No. 48 | No. 49 | No. 50 |
|---|---|---|---|---|---|---|---|---|---|---|---|---|
| 8,000 | ++~+++ | ++ | +++ | ++ | ++ | ++~+++ | ++ | ++ | ++ | ++ | +++ | +++ |
| 4,000 | ++ | ++ | ++ | ++ | +~++ | ++ | + | ++ | + | + | ++~ | ++ |

Table 1-continued (The results of the swelling test on garden peas)

| | | | | | | | | | | | | +++ | |
|---|---|---|---|---|---|---|---|---|---|---|---|---|---|
| 2,000 | + | +~± | ++ | + | +~± | + | ± | + | ± | + | | ++ | +~++ |
| 1,000 | +~± | +~± | + | + | ± | ± | ± | + | ± | ± | | + | + |

| Concent-ration (ppm) | No. 52 | No. 53 | No. 57 | No. 59 | No. 60 | No. 62 | No. 63 | No. 64 | No. 65 | No. 66 | Control (2-chloro-roethyl-phos-phonic acid) | β-hydro-xyethyl-hydra-Zine |
|---|---|---|---|---|---|---|---|---|---|---|---|---|
| 8,000 | ++ | ++~+++ | +~++ | ++ | +~++ | ++~+++ | +++ | +++ | ++ | ++ | +++ | ± |
| 4,000 | + | +~+ | ±~+ | + | + | — | ++ | ++~+++ | + | + | ++ | — |
| 2,000 | ± | ±~+ | ± | ± | + | + | + | ++ | + | ± | + | — |
| 1,000 | ± | ± | ± | ± | ± | + | + | + | ± | ± | + | — |

—: the rate of swelling on the basis of the non-treated lot being less than 5%
±: the rate of swelling 6 to 20%
+: the rate of swelling 21 to 40%
++: the rate of swelling 41 to 60%
+++: the rate of swelling 61 to 80%
++++: the rate of swelling 81 to 100%

Test Example 2

Pots with an inside diameter of 12 cm were filled with a field soil of volcanic ashes. Uniformly grown tomatoes (10 leaves) were transplanted in each of the pots. The pots were then allowed to stand in a greenhouse, and after the tomatoes set their roots firmly, the paste of the compound of this invention was coated on an aluminum foil in an amount of 0.1g or 0.05 g and applied to the fifth internode of the tomato plants. Five days after the application, the degree of epinasty was evaluated.

Table 2

| Compound Nos. | Amount applied (g) | Angle between the petiole and the stem |
|---|---|---|
| 7 | 0.1 | 115° |
|   | 0.05 | 82° |
| 8 | 0.1 | 124° |
|   | 0.05 | 90° |
| 21 | 0.1 | 114° |
|   | 0.05 | 76° |
| 49 | 0.1 | 110° |
|   | 0.05 | 77° |
| 2-Chloroethyl-phosphonic acid | 0.1 | 112° |
|   | 0.05 | 80° |
| Non-treated |   | 56° |

Test Example 3

Pots with an inside diameter of 12 cm were filled with a field soil of volcanic ashes, and uniformly grown tomatoes (10 grown leaves) were transplanted in each pot. The pots were allowed to stand in a greenhouse, and after they fully took roots, the wettable powder of the compound of this invention was dissolved in water to form dilutions with the desired concentration. 3 ml. of each of the dilutions was sprayed uniformly on the leaves and the stalk. Then, the tomatoes were grown for 20 days in a greenhouse, and the epinasty of the tomatoes, the action of forming adventitious roots, the defoliating action, and phytotoxicity were examined. The evaluation of the results was made on a scale of the following five grades.

Table 3

| | | Effects of treatment on tomatoes | | | |
|---|---|---|---|---|---|
| Compound | Concentration (ppm) | Epinasty | Formation of adventitious root | Defoliation | Phytotoxicity |
| 7 | 8,000 | +++ | +++ | ++ | — |
|   | 4,000 | +++ | ++ | + | — |
|   | 2,000 | ++ | + | + | — |
|   | 1,000 | + | + | ± | — |
| 8 | 8,000 | +++ | ++ | + | — |
|   | 4,000 | +++ | ++ | ±~+ | — |
|   | 2,000 | ++ | + | ± | — |
|   | 1,000 | + | ± | — | — |
| 21 | 8,000 | ++ | ++ | + | — |
|   | 4,000 | ++ | ++ | ± | — |
|   | 2,000 | + | + | ± | — |
|   | 1,000 | + | ± | — | — |
| 2-Chloroethylphosphonic acid (comparison) | 8,000 | +++ | +++ | ++ | ± |
|   | 4,000 | ++ | +++ | + | ± |
|   | 2,000 | + | ++ | ±~+ | — |
|   | 1,000 | + | + | ± | — |
| β-hydroxyethylhydrazine (comparison) | 8,000 | + | ± | + | — |
|   | 4,000 | — | — | — | — |

—: non-phytotoxicity
±: slight "
+: moderate "
++: extreme "
+++: severe "

Example 4

Unglazed pots with an inside diameter of 15 cm were filled with a field soil of volcanic ashes, and 12 French bean seeds were sown in each of the pots. Then, they were grown for about one week in a greenhouse. Eight uniformly grown plants were left, and the others were cut off by a scissors. When the second triple leaflets of the French beans were developed, the leaves and the stalk of the French beans were sprayed with 4 ml. of the wettable powder of the chemical of this invention diluted with water to each of the concentrations shown in Table 4. The evaluation was made on the same scale of five grades as in Test Example 1.

Table 4

| Compounds | Concentration (ppm) | Effects on French beans Growth inhibition | Epinasty | Yellowing | Defoliation | Disappearance of apical dominance |
|---|---|---|---|---|---|---|
| 49 | 4,000 | ++~+++ | +++ | +++ | +++ | +++ |
|  | 2,000 | + | ++~+++ | ++ | ++ | ++ |
|  | 1,000 | + | + | + | + | + |
| 50 | 4,000 | ++~+++ | +++ | +++ | +++ | +++ |
|  | 2,000 | ++ | ++~+++ | ++ | +~++ | ++ |
|  | 1,000 | + | + | + | + | +~++ |
| 52 | 4,000 | ++ | ++ | ++ | + | ++ |
|  | 2,000 | + | ++ | + | ± | + |
|  | 1,000 | ± | + | ± | ± | + |
| 63 | 4,000 | +++ | +++ | +++ | +++ | +++ |
|  | 2,000 | ++ | ++ | +~++ | ++ | ++ |
|  | 1,000 | + | ++ | + | +~++ | +~++ |
| 2-Chloroethyl-phosphonic acid (comparison) | 4,000 | +++ | +++ | +++ | +++ | +++ |
|  | 2,000 | ++ | ++ | ++ | ++ | ++ |
|  | 1,000 | ++ | + | + | ++ | — |
| β-hydroxyethyl-hydrazine (comparison) | 8,000 | ± | + | + | ± | ± |
|  | 4,000 | — | ± | ± | — | — |
|  | 2,000 | — | — | — | — | — |

Test Example 5

The wettable powder of this invention diluted with water to each of the concentrations shown in Table 5 was sprayed to the stalk and leaves of uniformly grown tobacco plants after 80 days from sowing and before flowering. The amount of the water diluted powder sprayed was 10 ml. per plant. The tobaccoes were then grown in a greenhouse, and three days after the treatment, the rate of falling of the tobacco flower buds was determined. Twenty days after the treatment, the degree of yellowing of the tobacco leaves was determined. The results are shown in Table 5.

Table 5

| Compounds | Treatment effect on tobaccoes Concentration (ppm) | Rate of falling flower buds (%) | Yellowing degree (%) |
|---|---|---|---|
| 3 | 2,000 | 100 | 80 |
|  | 1,000 | 100 | 50 |
|  | 500 | 100 | 40 |
| 7 | 2,000 | 100 | 80 |
|  | 1,000 | 100 | 62 |
|  | 500 | 100 | 50 |
| 8 | 2,000 | 100 | 82 |
|  | 1,000 | 100 | 50 |
|  | 500 | 100 | 34 |
| 21 | 2,000 | 100 | 60 |
|  | 1,000 | 80 | 40 |

Table 5-continued

| Compounds | Treatment effect on tobaccoes Concentration (ppm) | Rate of falling flower buds (%) | Yellowing degree (%) |
|---|---|---|---|
|  | 500 | 40 | 20 |
| 49 | 2,000 | 100 | 74 |
|  | 1,000 | 100 | 53 |
|  | 500 | 95 | 23 |
| 63 | 2,000 | 100 | 65 |
|  | 1,000 | 86 | 42 |
|  | 500 | 62 | 24 |
| 2-Chloro-ethylphos-phonic acid (Comparison) | 2,000 | 100 | 80 |
|  | 1,000 | 82 | 60 |
|  | 500 | 54 | 32 |
| BOH (Comparison) | 2,000 | 44 | 40 |
|  | 1,000 | 16 | 13 |
|  | 500 | 5 | 8 |
| Non-treated | 0 | 0 | 7.5 |

Test Example 6

Coloration Test on Oranges:-

Mandarine oranges (Unshu variety) having a color resembling the bright color of the lower back of a firefly were coated with 2 ml. of each of water-diluted emulsions of this invention in each of the concentrations shown in Table 6, and allowed to stand in a constant temperature chamber at 10° C. On the tenth day after the treatment, the degree of coloration was observed. The test results were indicated as average values of five oranges in each lot. The evaluation was made on the following scale. The results are shown in Table 6.

Table 6

| Concentration (ppm) | Promotion of the coloration of oranges Compound No. 3 | No. 7 | No. 8 | No. 14 | No. 21 | No. 49 | No. 50 |
|---|---|---|---|---|---|---|---|
| 2,000 | 5 | 5 | 5 | 4.5 | 5 | 5 | 5 |
| 1,000 | 4.5 | 5 | 5 | 3.5 | 4.5 | 5 | 5 |
| 500 | 4 | 4.5 | 4.5 | 3.5 | 4 | 4 | 4.5 |

| Concentration (ppm) | No. 63 | No. 33 | No. 27 | No. 69 | No. 70 | 2-Chloro-ethylphos-phonic acid (comparison) | β-Hydro-xyethyl-hydrazine (comparison) | Non-treated |
|---|---|---|---|---|---|---|---|---|
| 2,000 | 5 | 5 | 5 | 5 | 5 | 5 | 3 | 1.5 |
| 1,000 | 5 | 4.5 | 4.5 | 4 | 4 | 4 | 2 |  |
| 500 | 4 | 4 | 4 | 3.5 | 3.5 | 3.5 | 1.5 |  |

0: Coloration before the treatment
1: Colored 20%
2: Colored 40%
3: Colored 60%
4: Colored 80%
5: Completely colored

Text Example 7

50 ml. of an aqueous solution of the emulsifiable concentrate of this invention in each of the concentrations indicated in Table 7 was sprayed uniformly all over the stalk and leaves of three-year old nut trees (1.5 m high). Fifteen days after the treatment, the degree of defoliation was examined. The results are shown in Table 7.

Table 7

| Compounds Nos. | Concentration (ppm) | | |
|---|---|---|---|
| | 10,000 | 5,000 | 2,500 |
| 3 | 100 | 85 | 65 |
| 8 | 100 | 100 | 70 |
| 14 | 100 | 80 | 60 |
| 21 | 100 | 80 | 75 |
| 49 | 98 | 60 | 30 |
| 63 | 100 | 62 | 40 |
| Comparison* | 100 | 70 | 52 |
| Comparison** | 5 | 0 | 0 |

*2-Chloroethylophosphonic acid
**β-hydroxyethylhydrazine

Test Example 8

A 10% w/v solution of the chemical of this invention in a coconut oil was coated on the leaves of a three-year old Ficus elastica tree. Two days later, the coated leaf blades were cut at the site of the petiole. The latex oozing out from the cuts was allowed to penetrate in a filter paper whose weight had been measured. The filter paper was then dried in the air, and its weight was measured. The yield of the latex obtained from ten leaves with respect to each concentration was divided by the weight of the leaves, and expressed is percentages based on the value obtained with the nontreated group. The results are shown in Table 8.

Table 8

| Compounds Nos. | Percentages |
|---|---|
| 3 | 132 |
| 7 | 140 |
| 8 | 153 |
| 21 | 135 |
| 49 | 138 |

Table 8-continued

| Compounds Nos. | Percentages |
|---|---|
| 63 | 134 |
| 2-Chloromethylphosphonic acid | 139 |
| Non-treated | 100 |

Test Example 9

A 10% w/v solution of the chemical of this invention in a coconut oil was coated in a tape form with a width of 5 cm immediately below an extracting cut provided on the trunk of Hevea brasiliensis. Every other day, an extracting cut in a semi-helical shape was provided, and the yield of dry rubber obtained over a period of two weeks was measured. The results are shown in Table 9. The values in the table are precentages based on the control (coating of a coconut oil alone).

Table 9

| Compounds Nos. | Percentages |
|---|---|
| 3 | 145 |
| 7 | 152 |
| 8 | 162 |
| 49 | 150 |
| 2-Chloromethylphosphonic acid | 156 |
| Coconut oil | 100 |

Test Example 10

The swelling test on young garden peas was performed in the same way as in Test Example 1 except that the amount of the chemical applied to the leaves and the stalk was changed to 1 ml. in the concentration shown in Table 10. The results were evaluated on a scale of five grades as follows:

Table 10

| Concentration (mol/l) | Test Chemicals (Compounds Nos) | | | | | | | | | 2-Chloroethyl-sulfonic acid (comparison) |
|---|---|---|---|---|---|---|---|---|---|---|
| | No. 38 | No. 39 | No. 40 | No. 41 | No. 42 | No. 43 | No. 44 | No. 45 | No. 46 | |
| $5 \times 10^{-2}$ | +++ | ++ | ++ | +~++ | ++ | +++ | ++ | +~++ | ++ | +++ |
| $2.5 \times 10^{-2}$ | +++ | ++ | + | + | + | +++ | + | + | + | +++ |
| $10^{-2}$ | ++ | + | + | + | + | ++ | + | ± | ± | ++ |
| $5 \times 10^{-3}$ | ++ | ± | ± | ± | ± | + | ± | ± | ± | + |
| $10^{-3}$ | + | ± | ± | ± | ± | + | ± | − | − | ± |

−: no action
±: small effect
+: intermediate effect
++: somewhat great effect
+++: very great effect

Test Example 11

The effects on tomatoes were tested in the same way as in Test Example 3 by using the chemicals in the concentrations shown in Table 11. The results are shown in Table 11.

Table 11

| Chemicals | Concentration (mol/l) | Epinasty | Formation of adventitious root | leaf fall | Phytotoxicity |
|---|---|---|---|---|---|
| Compound No. 38 | $5 \times 10^{-2}$ | +++ | +++ | ++ | − |
| | $10^{-2}$ | +++ | ++ | + | − |
| | $5 \times 10^{-3}$ | ++ | + | + | − |
| | $10^{-3}$ | + | + | ± | − |
| Compound No. 41 | $5 \times 10^{-2}$ | ++ | ++ | + | − |
| | $10^{-2}$ | ++ | + | ± | − |
| | $5 \times 10^{-3}$ | + | + | ± | − |
| | $10^{-3}$ | ± | ± | − | − |
| 2-Chloroethyl- | $5 \times 10^{-2}$ | +++ | +++ | ++ | + |

Table 11-continued

| Chemicals | Concentration (mol/l) | Epinasty | Formation of adventitious root | leaf fall | Phytotoxicity |
|---|---|---|---|---|---|
| phosphonic acid (comparison) | $10^{-2}$ | ++ | +++ | + | ± |
|  | $5 \times 10^{-3}$ | + | ++ | ± | − |
|  | $10^{-3}$ | ± | + | ± | − |

Example 12

The effects on tobacco plants were tested in the same way as in Test Example 5 by using the chemicals in the concentrations shown in Table 12. The results are shown in Table 12.

Table 12

| Test Chemicals | Concentration (mol/l) | Falling of flower buds (%) (one day after treatment | Yellowing rate (%) (20 days after treatment) |
|---|---|---|---|
| Compound No. 38 | $10^{-2}$ | 100 | 75 |
|  | $10^{-3}$ | 100 | 50 |
|  | $10^{-4}$ | 100 | 40 |
| Compound No. 41 | $10^{-2}$ | 100 | 60 |
|  | $10^{-3}$ | 95 | 40 |
|  | $10^{-4}$ | 60 | 25 |
| Compound No. 43 | $10^{-2}$ | 100 | 75 |
|  | $10^{-3}$ | 100 | 50 |
|  | $10^{-4}$ | 90 | 40 |
| Compound No. 44 | $10^{-2}$ | 100 | 50 |
|  | $10^{-3}$ | 75 | 30 |
|  | $10^{-4}$ | 40 | 20 |
| 2-Chloroethylphosphonic acid (comparison) | $10^{-2}$ | 100 | 75 |
|  | $10^{-3}$ | 85 | 60 |
|  | $10^{-4}$ | 50 | 30 |

Test Example 13

Tomatoes, ripe but not yet colored, were harvested, and the wettable powders of this invention diluted with water to the concentrations shown in Table 13 were coated in an amount of 2 ml. on the skins of the tomatoes. The coated tomatoes were allowed to stand indoors for 10 days, and then the degree of coloration was determined. The results are shown in Table 13.

Table 13

| Concentration (mol/l) | Chemicals | | |
|---|---|---|---|
|  | Compound No. 38 | Compound No. 41 | 2-Chloroethylphosnonic acid (comparison) |
| $10^{-2}$ | +++ | +++ | +++ |
| $5 \times 10^{-3}$ | ++ | ++ | + |
| $10^{-3}$ | ++ | + | ± |

Test Example 14

One week before the full flowering of persimmons (variety Fuyu), an aqueous solution each of the wettable powder of this invention and 2-chloroethylphosphonic acid (comparison) was sprayed in the concentration given in Table 14 to all over the trees. The test results were investigated 20 days after the treatment, and the fruit-bearing rate and the fruit-to-leaf ratio were determined. The results are shown in Table 14. The fruit-to-leaf ratio shows the balance between the number of leaves and the number of fruits, and indicates the number of fruits per leaf.

Table 14

| Chemicals | Concentration (ppm) | Fruit-bearing rate (%) | Fruit-to-leaf ratio |
|---|---|---|---|
| Compound No. 38 | 30 | 25.2 | 20.1 |
|  | 50 | 21.8 | 23.5 |
|  | 75 | 13.8 | 30.6 |
| 2-Chloroethyl-phosphonic acid (Comparison) | 30 | 38.0 | 13.8 |
|  | 50 | 26.2 | 16.1 |
|  | 75 | 23.4 | 20.2 |
| Non-treated (comparison) |  | 39.2 | 13.0 |

These results demonstrate that the chemical of this invention can lead to fruit harvesting to a degree near the ideal fruit-to-leaf ratio (20 to 25) in the cultivation of Fuyu persimmons, and can markedly save the labor of picking fruits.

Test Example 15

An aqueous solution of the liquid preparation of this invention in each of the concentrations indicated in Table 15 was sprayed all over the stem and leaves of pineapples (variety, Singapore Spanish) in an amount of 50 ml. per pineapple plant. 50 days after the treatment, the rate of flowering (the number of pineapples taking flowers to that of pineapples treated) was determined. Ten pineapples were grown per lot. The results are shown in Table 15.

Table 15

| Chemicals | Concentrations (ppm) | Rate of flowering | Average fruit weight (g) |
|---|---|---|---|
| Compound No. 41 | 200 | 10/10 | 850 |
|  | 400 | 10/10 | 903 |
|  | 800 | 10/10 | 905 |
| 2-Chloroethyl-phosphonic acid (comparison) | 200 | 7/10 | 840 |
|  | 400 | 9/10 | 850 |
|  | 800 | 10/10 | 900 |
| Carbide (comparison) | Conventional method | 6/10 | 780 |

Test Example 16

Mandarine oranges (variety, Unshu) having a color resembling the bright color of the lower back of a firefly were immersed for 3 minutes in an aqueous solution of the emulsifiable concentrate of this invention in each of the concentrations shown in Table 16, withdrawn, and then allowed to stand indoors for 5 hours. Then, they were thoroughly washed with water, and dried in air. Ten days after the treatment, the acidity of the orange was measured, and the state of coloration was observed. The test results were expressed as average valves of five oranges in one lot. The state of coloration was evaluated on the same scale as in Test Example 6.

Table 16

| Chemicals | Concentration (ppm) | Acidity (pH) | State of coloration |
|---|---|---|---|
| Compound No. 41 | 500 | 3.45 | 4.5 |
|  | 1000 | 3.48 | 5 |
|  | 2000 | 3.60 | 5 |
| 2-Chloroethyl-phosphonic acid (comparison) | 500 | 3.46 | 3.5 |
|  | 1000 | 3.45 | 4 |
|  | 2000 | 3.50 | 5 |
| Non-treated |  |  |  |

Table 16-continued

| Chemicals | Concentration (ppm) | Acidity (pH) | State of coloration |
|---|---|---|---|
| (comparison) | | 3.40 | 2.5 |

Test Example 17

Cucumbers (variety, Otone No. 1) in the four-leaf stage were sprayed at their stem and leaves with 10 ml. of an aqueous solution each of the wettable powders of this invention in the concentrations shown in Table 17, and were grown in a greenhouse. The percentage of the number of pistils which adhered based on the total number of flowers was examined. The results were expressed as averages of four pieces per lot. The results are shown in Table 17.

Table 17

| Chemicals | Concentration (ppm) | Rate of pistil adhesion at the main branch (%) | Rate of pistil adhesion at the 1st node of the side branch (%) | Rate of pistil adhesion at the 2nd node of the side branch (%) | Yield ratio |
|---|---|---|---|---|---|
| Compound No. 38 | 200 | 50.3 | 66.4 | 35.2 | 140 |
| | 100 | 38.4 | 62.0 | 32.5 | 130 |
| | 50 | 20.5 | 57.0 | 20.4 | 130 |
| Compound No. 41 | 200 | 45.3 | 64.6 | 31.5 | 120 |
| | 100 | 38.6 | 60.5 | 30.3 | 108 |
| | 50 | 18.2 | 57.0 | 20.6 | 105 |
| 2-Chloro-ethyl-phosphonic acid (comparison) | 200 | 44.8 | 65.6 | 32.4 | 135 |
| | 100 | 38.5 | 60.3 | 30.5 | 105 |
| | 50 | 15.0 | 56.4 | 20.7 | 103 |
| Non-treated (comparison) | | 7.6 | 88.6 | 4.5 | 100 |

Test Example 18

An aqueous solution of the emulsifiable concentrate of this invention in each of the concentrations shown in Table 18 was sprayed all over the stems leaves of a chestnut tree (3 years old; 1.0 to 1.5 m in height) in an amount of 50 ml. and of a small-sized persimmon trees in an amount of 5 ml. Fifteen days after the treatment, the rate of leaf falling was examined. The rate of leaf falling of 100% means that all the leaves fell, and the rate of leaf falling of 0% means that no leaf fell. The results are shown in Table 18.

Table 18

| Chemicals | Concentration (ppm) | Rate of leaf falling (%) Chestnut | Small-sized persimmon |
|---|---|---|---|
| Compound No. 38 | 10000 | 100 | 100 |
| | 5000 | 60 | 85 |
| | 2500 | 35 | 50 |
| 2-Chloroethyl-phosphonic acid (comparison) | 10000 | 85 | 100 |
| | 5000 | 50 | 60 |
| | 2500 | 20 | 45 |

Test Example 19

The swelling test on young garden peas was performed in the same way as in Test Example 10 using the chemicals in the concentrations given in Table 19. The results are shown in Table 19.

Table 19

| Concentration (ppm) | Compound No. 73 | Compound No. 74 | Compound No. 75 | Compound No. 76 | Compound No. 81 |
|---|---|---|---|---|---|
| 10,000 | +++ | ++ | +++ | ++ | ++ |
| 5,000 | ++ | + | +++ | + | + |
| 2,500 | + | ± | ++ | + | ± |
| 1,000 | + | ± | + | ± | − |

Test Example 20

Pots with an inside diameter of 12 cm were filled with a field soil of valcanic ashes, and uniformly grown French beans (with vines) were transplanted, two in each pot. The pots were allowed to stand in a greenhouse, and after the French been plants took root, the wettable powder of this invention diluted with water to each of the concentrations shown in Table 20 was uniformly sprayed to the stalks and leaves of the plants in an amount of 2 ml. The plants were then grown for 10 days in the greenhouse, and then the epinasty, yellowing and leaf falling of the plants were observed. The evaluation of the effect was expressed on the same scale as in Test Example 10, and the phytotoxicity was evaluated on the same scale as in Test Example 3. The results are shown in Table 20.

Table 20

| Chemical | Concentration (ppm) | Epinasty | Yellowing | Leaf fall | Phytotoxicity |
|---|---|---|---|---|---|
| Compound No. 73 | 8,000 | +++ | ++ | ++ | − |
| | 4,000 | ++ | + | + | − |
| | 2,000 | + | ± | + | − |
| Compound No. 75 | 8,000 | +++ | ++ | ++ | − |
| | 4,000 | ++ | + | + | − |
| | 2,000 | ++ | ± | + | − |
| 2-Chloro-ethyl-phosphonic acid (comparison) | 8,000 | +++ | ++ | ++ | + |
| | 4,000 | +++ | + | ++ | ± |
| | 2,000 | ++ | + | + | − |

Test Example 21

The test on tobacco plants was performed in the same way as in Example 5. The results are shown in Table 21.

Table 21

| Chemicals | Concentration (ppm) | Falling of flower buds (%) one day after the treatment | Yellowing rate (%) 20 days after treatment |
|---|---|---|---|
| Compound No. 73 | 4000 | 100 | 70 |
| | 2000 | 80 | 40 |
| | 1000 | 60 | 20 |
| Compound No. 75 | 4000 | 100 | 70 |
| | 2000 | 65 | 35 |
| | 1000 | 40 | 20 |
| Non-treated | − | 0 | 0 |

Test Example 22

The coloration test on mandarine oranges was performed in the same way as in Test Example 6 using each of the compounds shown in Table 22 in the concentrations indicated. The results are shown in Table 22.

Table 22

| Chemicals | Concentration (ppm) | Acidity (pH) | State of coloration |
|---|---|---|---|
| Compound | 4000 | 3.50 | 5 |

Table 22-continued

| Chemicals | Concentration (ppm) | Acidity (pH) | State of coloration |
|---|---|---|---|
| No. 73 | 2000 | 3.48 | 4.5 |
|  | 1000 | 3.60 | 4.5 |
| Compound | 4000 | 3.46 | 5 |
| No. 75 | 2000 | 3.60 | 5 |
|  | 1000 | 3.50 | 4.5 |
| 2-Chloroethyl- | 4000 | 3.50 | 5 |
| phosphonic | 2000 | 3.60 | 5 |
| acid | 1000 | 3.55 | 4.5 |
| (comparison) |  |  |  |
| Non-treated | — | 3.60 | 2.5 |

Test Example 23

The effect of accelerating the leaf falling of chestnuts was tested in the same way as in Test Example 18 using each of the compounds shown in Table 23 in the concentrations indicated. The results are shown in Table 23.

Table 23

| Chemicals | Concentration (ppm) | Rate of leaf falling (%) |
|---|---|---|
| Compound | 5000 | 50 |
| No. 73 | 2500 | 30 |
| Compound | 5000 | 65 |
| No. 75 | 2500 | 40 |
| 2-Chloro- | 5000 | 60 |
| ethylphos- |  |  |
| phonic acid | 2500 | 40 |
| (comparison) |  |  |
| Non-treated | — | 0 |

What we claim is:

1. A compound of the formula

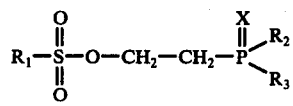

wherein $R_1$ is a member selected from the group consisting of substituted or unsubstituted $C_1$ to $C_{12}$ linear- or branched-alkyl $C_5$ to $C_{12}$ cyclo-alkyl, substituted or unsubstituted $C_2$ to $C_{12}$ linear-or branched- alkenyl or $C_5$ to $C_{12}$ cycloalkenyl and substituted or unsubstituted $C_6$ to $C_{14}$ carbocyclic aryl; $R_2$ and $R_3$ are identical or different and each represents a group or an atom selected from the group consisting of (1) -OR' in which R' is a member selected from the group consisting of a hydrogen atom, substituted or unsubstituted $C_1$ to $C_{12}$ linear- of branched- alkyl or $C_5$ to $C_{12}$ cycloalkyl, substituted or unsubstituted $C_2$ to $C_{12}$ linear- or branched- alkenyl or $C_5$ to $C_{12}$ cycloalkenyl and substituted or unsubstituted $C_6$ to $C_{14}$ carbocyclic aryl, (2) -SR' in which R' is as defined above, (3) -N(R')$_2$ in which R' is the same as defined above and the two R' groups are identical or different, and (4) a halogen atom; and X is S or O; the substituent for the substituted alkyl group or the substituted alkenyl group is a member selected from the group consisting of halogen atoms, cyano, nitro, alkoxycarbonyl with the alkoxy moiety containing 1 to 12 carbon atoms, alkoxy of 1 to 12 carbon atoms, carboxyl, alkanoyl of 1 to 12 carbon atoms, alkanoyloxy of 1 to 12 carbon atoms, benzoyloxy, thio-cyanato, isothiocyanato, acetamide, acetylthio, phosphono, β-phosphonoethyloxysulfonyl, $(CH_3)_3 \overset{+}{N}{}^{Cl} - CH_2-CH_2-$, phenyl, phenylalkyl of 7 to 14 carbon atoms, and alkylthio with the alkyl moiety containing 1 to 12 carbon atoms; and the substituent for the substituted aryl group is a member selected from the group consisting of alkyl of 1 to 6 carbon atoms, halogen atoms, acetyl, acetamido, nitro, cyano, carboxyl, alkoxy of 1 to 6 carbon atoms and hydroxyl; with the proviso that when X is O and both $R_2$ and $R_3$ are the group -OR', at least one of —OR' groups is -OH, and when X is S, both $R_2$ and $R_3$ are not the groups —N(R')$_2$ at the same time.

2. A method for regulating the growth of plants which comprises applying to a plant or to the locus in which a plant is growing or is to be grown, a plant growth regulating amount of a compound according to claim 1.

3. A plant growth regulating composition which comprises a plant growth regulating amount of a compound according to claim 1 and a gaseous, liquid or solid diluent therefor.

4. A plant growth regulating composition according to claim 20 which consists of about 0.00001% to about 99% based on the weight of the regulator, of said compound of claim 1 and a gaseous, liquid or solid diluent therefor.

5. A method according to claim 2 wherein the amount of said compound to be applied to the plant is 2 to 100 ml. per plant with the regulator concentration of about 10 to about 10,000 ppm.

6. A method according to claim 2 wherein the amount of said compound to be applied to the locus in which the plant is growing or will be grown is about 10 to about 4,000 g/10 ares.

7. A method according to claim 2 wherein the application of the compound to the plant is performed by emersing the plant in a liquid preparation of the compound in a concentration of about 10 to about 10,000 ppm. for a period of from about 3 minutes to about 6 hours.

* * * * *

UNITED STATES PATENT AND TRADEMARK OFFICE
CERTIFICATE OF CORRECTION

PATENT NO. : 4,059,431

DATED : November 22, 1977

INVENTOR(S) : Tetsuo Takematsu, Makoto Konnai, Makoto Takeda, Nobuhiko Fuga, Kaoru Ikeda and Kiyoshi Shugaya It is certified that error appears in the above-identified patent and that said Letters Patent are hereby corrected as shown below:

Column 22, line 44, correct "Nimeral" to --Mineral--.

Column 35, line 48, correct "linear-of" to --linear-or--.

Column 36, line 12, correct "$(CH_3)_3^+N^{cl} - CH_2-CH_2-$" to --$(CH_3)_3\overset{\oplus}{N}Cl^{\ominus}-CH_2-CH_2-$ --.

Signed and Sealed this

Twenty-third Day of May 1978

[SEAL]

Attest:

RUTH C. MASON
Attesting Officer

LUTRELLE F. PARKER
Acting Commissioner of Patents and Trademarks